US006998250B2

(12) United States Patent
McMichael et al.

(10) Patent No.: US 6,998,250 B2
(45) Date of Patent: Feb. 14, 2006

(54) METHOD FOR DETECTING HELICOBACTER PYLORI

(75) Inventors: Donald J. McMichael, 10091 S. Eden Ridge Dr., South Jordan, UT (US) 84095; Kristy Peterson, 5164 Cottonwood La., Salt Lake City, UT (US) 84117; Barry J. Marshall, 40 Beatrice Road, Dalkeith, Western Australia (AU), 6009; Aruni H. W. Mendis, 109 Fairway Circle, Connolly, Western Australia (AU), 6027; Simon Chairman, 18 Retreat Circuit, Beaconsfield, Victoria (AU), 3807

(73) Assignees: Donald J. McMichael; Kristy Peterson; Barry J. Marshall; Aruni H. W. Mendis; Simon Chairman

( * ) Notice: Subject to any disclaimer, the term of this patent is extended or adjusted under 35 U.S.C. 154(b) by 514 days.

(21) Appl. No.: 09/977,667

(22) Filed: Oct. 15, 2001

(65) Prior Publication Data

US 2003/0082661 A1 May 1, 2003

(51) Int. Cl.
*C12Q 1/04* (2006.01)

(52) U.S. Cl. .............................. 435/34; 435/12; 435/30
(58) Field of Classification Search .................. 435/34, 435/12, 29, 30; 424/234.1; 514/925, 926, 514/927
See application file for complete search history.

(56) References Cited

U.S. PATENT DOCUMENTS

| | | | |
|---|---|---|---|
| 1,521,689 A | 1/1925 | King | |
| 3,145,086 A | 8/1964 | Free et al. | |
| 3,395,082 A | 7/1968 | Mast | |
| 3,411,723 A | 11/1968 | Kohn | |
| 3,461,036 A | 8/1969 | Harvill et al. | |
| 3,653,389 A | 4/1972 | Shannon | |
| 3,873,269 A | 3/1975 | Kraffczyk et al. | |
| D241,803 S | 10/1976 | Amiot | |
| 4,016,268 A | 4/1977 | Goldenberg et al. | |
| 4,016,865 A | 4/1977 | Fredricks | |
| 4,027,658 A | 6/1977 | Marshall | |
| 4,101,382 A | 7/1978 | Chang | |
| D249,772 S | 10/1978 | Amiot | |
| 4,132,502 A | 1/1979 | Bunke | |
| 4,153,685 A | 5/1979 | Serfontein | |
| 4,160,505 A | 7/1979 | Rauschenberger | |
| 4,226,328 A | 10/1980 | Beddow | |
| 4,282,316 A | 8/1981 | Modrovich | |
| 4,293,074 A | 10/1981 | Dunsky | |
| D266,434 S | 10/1982 | Kowalski | |
| D271,370 S | 11/1983 | San Antonio | |
| 4,620,548 A | 11/1986 | Hasselbrack | |
| D288,716 S | 3/1987 | Covell et al. | |
| 4,736,850 A | 4/1988 | Bowman et al. | |
| 4,748,113 A | 5/1988 | Marshall | |
| 4,777,947 A | 10/1988 | Zwick | |
| 4,803,983 A | 2/1989 | Siegel | |

(Continued)

FOREIGN PATENT DOCUMENTS

| | | |
|---|---|---|
| EP | 0018825 | 2/1985 |
| EP | 0365459 A1 | 4/1990 |
| EP | 369292 * | 5/1990 |
| EP | 0606651 A2 | 7/1994 |
| EP | 0721898 A1 | 7/1996 |
| EP | 0896547 B1 | 6/2002 |
| FR | 2442268 | 7/1980 |
| FR | 2654436 * | 5/1991 |
| GB | 1112251 | 5/1968 |
| GB | 1478742 | 7/1977 |
| GB | 2 037 811 | 7/1980 |
| JP | 58077663 A | 5/1983 |
| WO | 82/01646 | 5/1982 |
| WO | 89/09407 | 10/1989 |
| WO | 94/22380 | 10/1994 |
| WO | 98/54563 | 12/1998 |
| WO | 99/02101 | 1/1999 |
| WO | 99/25251 | 5/1999 |
| WO | 99/51769 | 10/1999 |
| WO | 99/61892 | 12/1999 |
| WO | WO 01/64543 | 9/2001 |

OTHER PUBLICATIONS

Roda, A. Development of a Chemiluminescent Urease Activty Assay for HP Infection Diagnosis in Gastric Mucosa Biopsies. Analytical Biochemistry 264, 47–52, 1998.*

U.S. Appl. No. 09/977,555, filed Oct. 15, 2001, Marshall et al., Method for the Detection of Urease and Method for Using Same.

U.S. Appl. No. 09/977,556, filed Oct. 15, 2001, Marshall et al., System for the Detection of Urease and Method for Using Same.

U.S. Appl. No. 10/026,321, filed Dec. 20, 2001, Marshall et al., Gel–Based Media for Transfer Slides, Methods of Producing and Using Same.

U.S. Appl. No. 09/977,874, filed Oct. 15, 2001, Marshall et al., Composition for the Detection of Gastrointestinal Disorders.

U.S. Appl. No. 09/977,546, filed Oct. 15, 2001, Marshall et al., Systems for Performing Multiple Diagnostic Tests.

*Primary Examiner*—Ralph Gitomer
(74) *Attorney, Agent, or Firm*—Sheldon H. Parker (57) ABSTRACT

A system and method for detecting bacterial infections in the gastrointestinal tract is disclosed. The system includes a carrier having a first well and a second well. A first composition is disposed in the first well and contains urea in powdered form. A second composition is disposed in a second well and contains an indicator. A biopsy of a gastric sample is manipulated with a specimen-handling tool and is first contacted with the first composition and then placed in the second composition. The second composition indicates the presence of an enzyme, which, in turn, indicates the presence of bacteria.

16 Claims, 9 Drawing Sheets

U.S. PATENT DOCUMENTS

| | | | |
|---|---|---|---|
| D301,371 S | 5/1989 | Kaprelian | |
| 4,829,006 A | 5/1989 | Smith et al. | |
| 4,830,010 A | 5/1989 | Marshall | |
| 4,923,801 A | 5/1990 | Marshall et al. | |
| 4,932,957 A | 6/1990 | Zwick | |
| 4,955,971 A | 9/1990 | Goulter | |
| 5,116,346 A | 5/1992 | Yeh | |
| D327,322 S | 6/1992 | Brewer, Jr. | |
| D328,347 S | 7/1992 | Santora | |
| 5,149,506 A | 9/1992 | Skiba et al. | |
| D331,800 S | 12/1992 | Han | |
| 5,182,191 A | 1/1993 | Fan et al. | |
| 5,228,201 A | 7/1993 | Atkins | |
| 5,238,651 A | 8/1993 | Chuba | |
| 5,256,684 A | 10/1993 | Marshall | |
| 5,258,178 A | 11/1993 | Cordle et al. | |
| 5,260,057 A | 11/1993 | Cordle et al. | |
| 5,304,540 A | 4/1994 | Blackburn et al. | |
| 5,314,804 A * | 5/1994 | Boguslaski et al. | 435/12 |
| 5,339,955 A | 8/1994 | Horan et al. | |
| 5,348,023 A | 9/1994 | McLucas | |
| 5,380,492 A | 1/1995 | Seymour | |
| 5,420,016 A * | 5/1995 | Boguslaski et al. | 435/12 |
| 5,431,884 A | 7/1995 | McDonough et al. | |
| 5,439,801 A * | 8/1995 | Jackson | 435/12 |
| 5,449,071 A | 9/1995 | Levy | |
| 5,479,019 A | 12/1995 | Gross | |
| 5,494,162 A | 2/1996 | Treace et al. | |
| 5,498,528 A * | 3/1996 | King | 435/34 |
| 5,501,597 A | 3/1996 | Wilson | |
| D368,520 S | 4/1996 | Brewer, Jr. | |
| 5,593,851 A * | 1/1997 | Jackson | 435/12 |
| 5,601,848 A | 2/1997 | Marshall | |
| 5,624,554 A | 4/1997 | Faulkner et al. | |
| 5,668,011 A * | 9/1997 | Jackson | 435/309.1 |
| 5,679,570 A * | 10/1997 | Heckenmuller et al. | 435/287.9 |
| 5,682,665 A | 11/1997 | Svanberg | |
| 5,702,911 A | 12/1997 | Whalen | |
| 5,709,838 A | 1/1998 | Porter et al. | |
| D390,659 S | 2/1998 | Chan et al. | |
| 5,722,422 A | 3/1998 | Palmer et al. | |
| D393,312 S | 4/1998 | Huttner | |
| 5,738,110 A | 4/1998 | Beal et al. | |
| 5,782,951 A | 7/1998 | Aylen et al. | |
| 5,846,488 A | 12/1998 | Richardson | |
| 5,846,751 A | 12/1998 | Pronovost et al. | |
| 5,854,013 A | 12/1998 | Ollar et al. | |
| 5,893,853 A | 4/1999 | Arnold | |
| D415,275 S | 10/1999 | Huttner | |
| 5,989,840 A | 11/1999 | D'Angelo et al. | |
| 5,997,567 A | 12/1999 | Cangelosi | |
| D419,238 S | 1/2000 | Maissami | |
| D420,133 S | 2/2000 | Huttner | |
| 6,039,959 A | 3/2000 | Burnie | |
| D423,669 S | 4/2000 | Huttner et al. | |
| 6,048,735 A | 4/2000 | Hessel et al. | |
| 6,060,241 A | 5/2000 | Corthésy-Theulaz | |
| 6,068,985 A | 5/2000 | Cripps et al. | |
| D428,489 S | 7/2000 | Huttner et al. | |
| D428,991 S | 8/2000 | Fourie et al. | |
| 6,113,875 A | 9/2000 | Nyström et al. | |
| 6,116,426 A | 9/2000 | Slonim | |
| D435,293 S | 12/2000 | Tang | |
| 6,156,346 A | 12/2000 | Chen et al. | |
| 6,165,736 A | 12/2000 | Fawcett | |
| 6,171,811 B1 | 1/2001 | Becerro De Bengoa Vallejo | |
| 6,172,215 B1 | 1/2001 | Keshi et al. | |
| 6,187,556 B1 * | 2/2001 | Lee et al. | 435/34 |
| D438,979 S | 3/2001 | Gomes et al. | |
| 6,228,605 B1 | 5/2001 | Marshall | |
| D445,503 S | 7/2001 | Huttner | |
| D447,237 S | 8/2001 | Huttner et al. | |
| 6,270,514 B1 | 8/2001 | McDonald | |
| 6,291,234 B1 | 9/2001 | Raz et al. | |
| 6,294,151 B1 | 9/2001 | Hayakawa et al. | |
| 6,309,818 B1 | 10/2001 | Malinda et al. | |
| D452,936 S | 1/2002 | Grisoni | |

OTHER PUBLICATIONS

U.S. Appl. No. 09/977,539, filed Oct. 15, 2001, McMichael et al., Methods for Performing Multiple Diagnostic Tests.

U.S. Appl. No. 09/977,547, filed Oct. 15, 2001, Peterson et al., Systems for Diagnostic Testing.

Abstract EP 07211898 A1, Neumeyer E S, Jul. 17, 1996.

* cited by examiner

METHOD FOR DETECTING HELICOBACTER PYLORI

The present invention relates generally to diagnostic testing for *Helicobacter pylori*.

When a patient is showing symptoms of a gastrointestinal disorder, it is beneficial to rapidly and accurately diagnose the disorder. Diagnostic testing is frequently performed in such situations to determine if a particular medical condition is present in that patient, including, for example, a bacterial infection.

Many ailments of the gastrointestinal system in humans are caused at least in part by bacteria. Some examples of such ailments are chronic or atrophic gastritis, gastroenteritis, non-ulcer dyspepsia, esophageal reflux disease, gastric motility disorders, peptic ulcers including gastric and duodenal ulcers, and the like. Bacteria that can cause these types of ailments include those of the genus *Campylobacter*, and particularly *Helicobacter pylori*. For example, *Helicobacter pylori* can cause bacterial infections on the mucosal surface of the gastrointestinal tract, particularly on the surface of the stomach. *Helicobacter pylori* is a gram-negative spiral organism which produces the enzyme urease. The organism may be found in the upper gastrointestinal tract that includes the esophagus, the stomach, the duodenum, the jejunum and the ileum.

Diagnostic testing systems are manufactured to test for a wide variety of conditions in numerous types of samples, such as, for example, blood, tissue biopsies, and saliva. Such testing systems may be utilized to determine the presence of particular bacteria, such as *Helicobacter pylori*. Some tests that have been proposed to detect *Helicobacter pylori* include those that are disclosed in numerous U.S. Patents, including, for example, U.S. Pat. No. 4,748,113 to Marshall, U.S. Pat. No. 5,314,804 to Boguslaski et al., U.S. Pat. No. 5,439,801 to Jackson, U.S. Pat. No. 5,702,911 to Whalen, U.S. Pat. No. 5,989,840 to D'Angelo et al., U.S. Pat. No. 6,068,985 to Cripps et al., U.S. Pat. No. 6,156,346 to Chen et al., and U.S. Pat. No. 6,187,556 to Lee et al., each of such patents being incorporated in their entirety by reference herein.

*Helicobacter pylori* produces an enzyme called urease. Various tests detect the presence of urease on a sample, such as, for example, a gastric sample that is obtained through endoscopy. In the tests described above, other biological samples may be used, such as, for example, blood, saliva, or urine. When urease is contacted with urea, a naturally occurring product of protein metabolism that has the chemical formula $H_2NCONH_2$, the urea hydrolyzes to form ammonium carbonate, which then decomposes into ammonia and carbon dioxide.

A sample of gastric material may be contacted with a composition containing urea and at least one indicator such as, for example, a pH indicator that changes color when there is a rise in pH. If urease is present within the gastric material, the urease breaks down the urea, which subsequently forms ammonia and causes the pH indicator to change color.

Some reagents, such as urease, that are used in some tests have a limited shelf life due to the tendency of such reagents to degrade. Tests that have a long shelf life enable medical facilities to increase their efficiencies and flexibility to purchase, store and administer such tests.

Various embodiments of the present invention are directed to a diagnostic system for diagnostic testing including a carrier having a first well and a second well. A first composition may be disposed in the first well of the carrier. The first composition may include urea in powdered form, the urea being capable of being converted into ammonia when contacted with urease. The second composition may include an indicator, the indicator being configured to indicate the presence of ammonia.

A specimen-handling tool may be disposed about at least a portion of one of the wells. The specimen-handling tool may be disposed within a cavity formed in the carrier. The specimen-handling tool may be adapted to manipulate a specimen such as a biopsy sample. An overlying member may be provided and may be disposed adjacent to the top surface of the carrier. The overlying member may be positioned over at least a portion of one or more of the wells and/or the cavity.

The specimen-handling tool may include a pair of cooperating arms. Each arm may include a tip portion and a rear portion, the arms being joined to each other at their rear portions. Each arm may further include a rearward arcuate portion, a forward arcuate portion, and an intermediate arcuate portion that is disposed between the rearward arcuate portion and the forward arcuate portion. The arcuate portions may be configured so that the area disposed between the pair of arms is approximately hourglass in shape.

The present invention also includes a method for detecting the presence of urease in a gastrointestinal system including grasping a sample of gastric material with a specimen-handling tool and contacting the gastric material with a first composition disposed in a first well of a carrier. The first composition may include urea, the urea being capable of being converted into ammonia when contacted with urease. The gastric material may be contacted with a second composition disposed in a second well of a carrier, the second composition including an indicator, the indicator being configured to indicate the presence of ammonia thereby indicating the presence of urease in the gastric material.

The present invention further includes a system for diagnostic testing including a carrier having a first well, and a composition for the detection of *Helicobacter pylori* disposed within the first well. A specimen-handling tool may be disposed about at least a portion of the first well. The composition for the detection of *Helicobacter pylori* including urea in powdered form, the urea being capable of being converted into ammonia when contacted with urease. The composition may further include and anti-caking agent and an indicator configured to indicate the presence of ammonia, such as, for example, phenol red.

Figure 1:
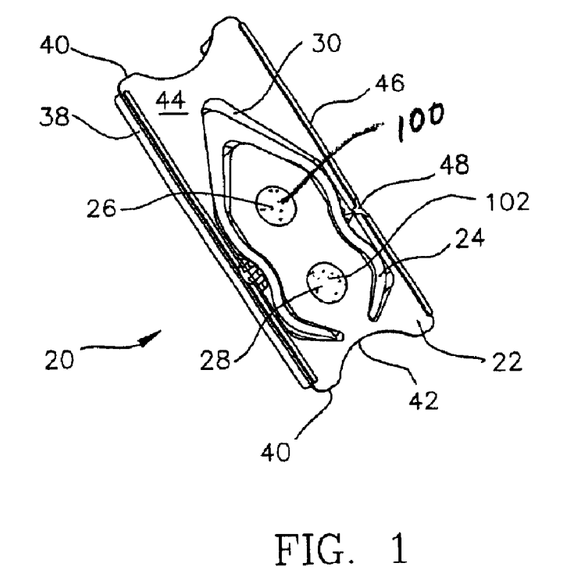
FIG. 1 is a perspective view of an embodiment of the system, carrier and specimen-handling tool of the present invention.
Figure 6:
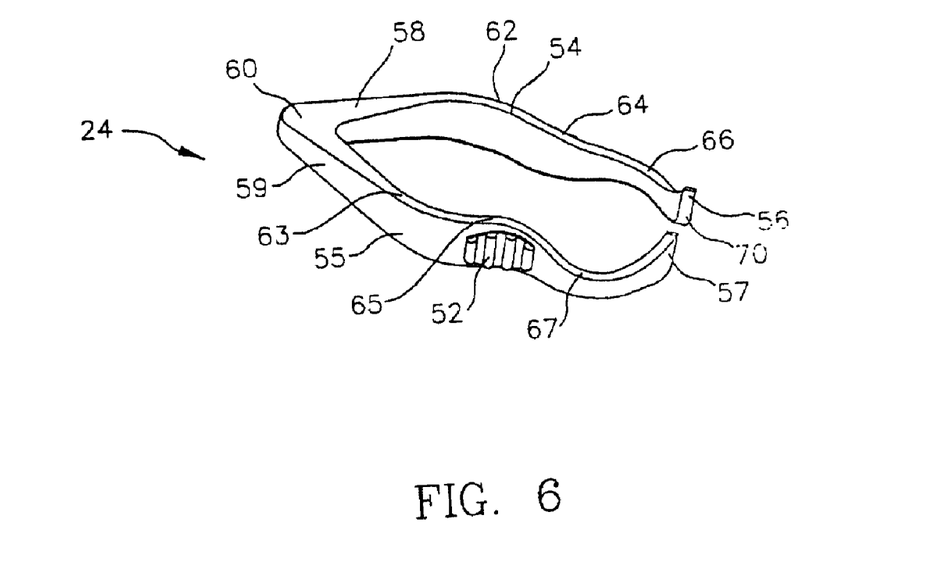
FIG. 6 is a perspective view of an embodiment of the specimen-handling tool of the present invention.
Figure 7:
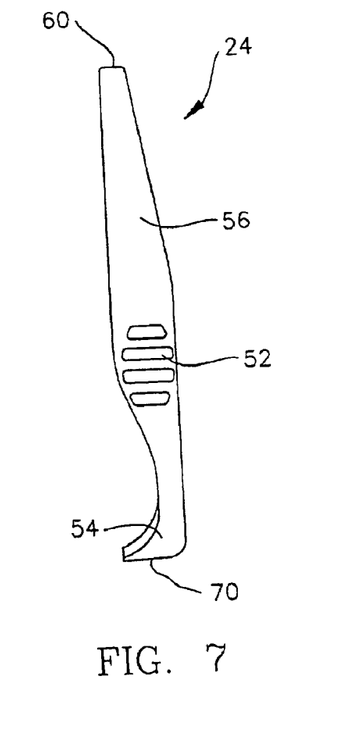
FIG. 7 is a side view of an embodiment of the specimen-handling tool of the present invention depicted in FIG. 6.
Figure 10:
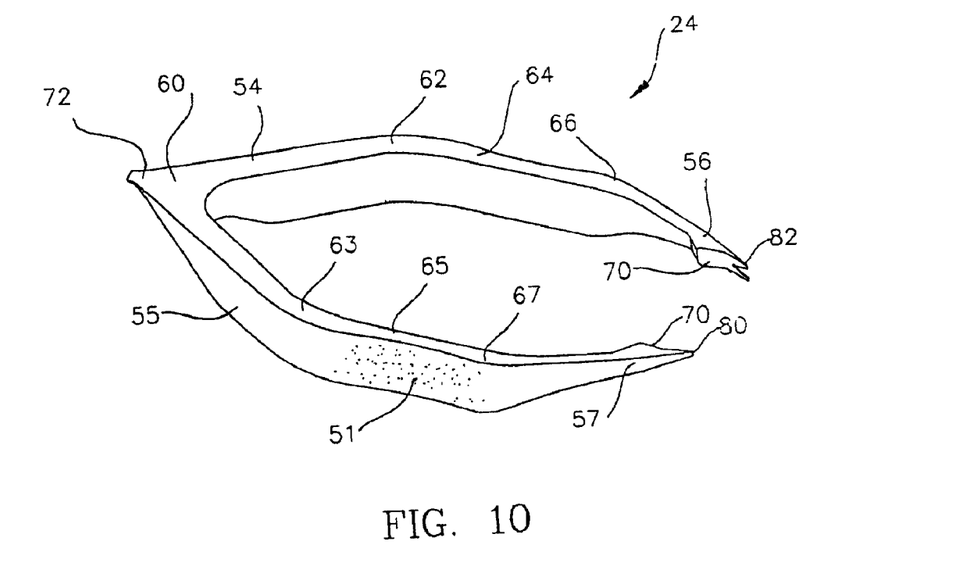
FIG. 10 is a perspective view of yet another embodiment of the specimen-handling tool of the present invention.
Figure 15:
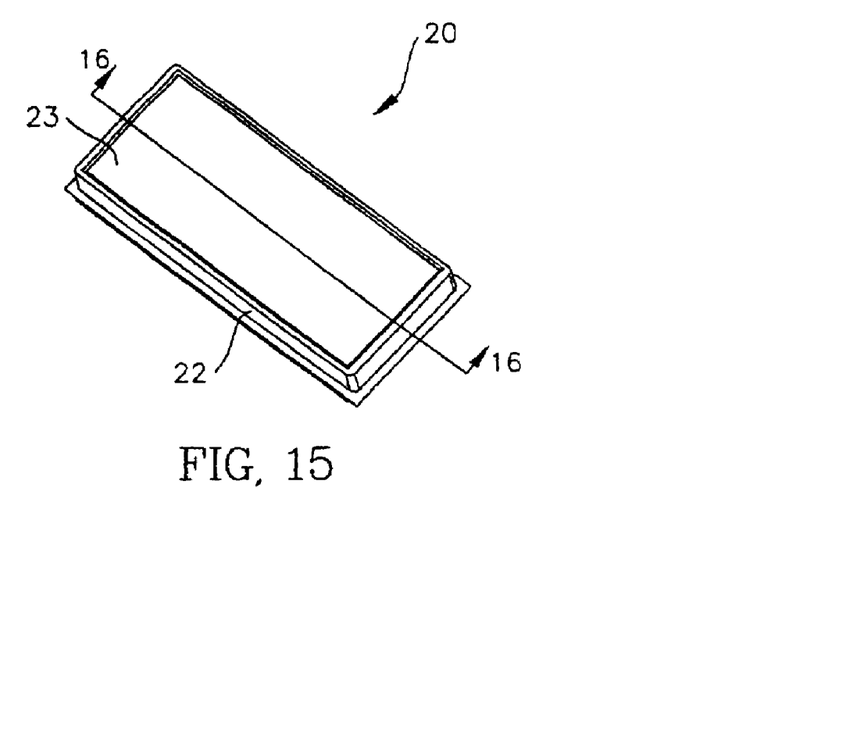
FIG. 15 is a perspective view of an embodiment of the system of the present invention.

The present invention is directed to systems and methods for detecting bacteria, such as, for example, *Helicobacter pylori*. FIG. 1 discloses an embodiment of a diagnostic system 20 according to the present invention that may be utilized for many types of diagnostic testing. Such diagnostic tests utilize a biological test specimen such as, for example, tissue biopsy, blood or saliva. The diagnostic system 20 may include a carrier 22 and a mechanism by which a user may manipulate a sample of tissue, such as, for example, the specimen-handling tool 24 that is shown in FIGS. 1, 6 and 10. As depicted in FIG. 15, the diagnostic system 20 may further include an overlying member 23.

Figure 2:
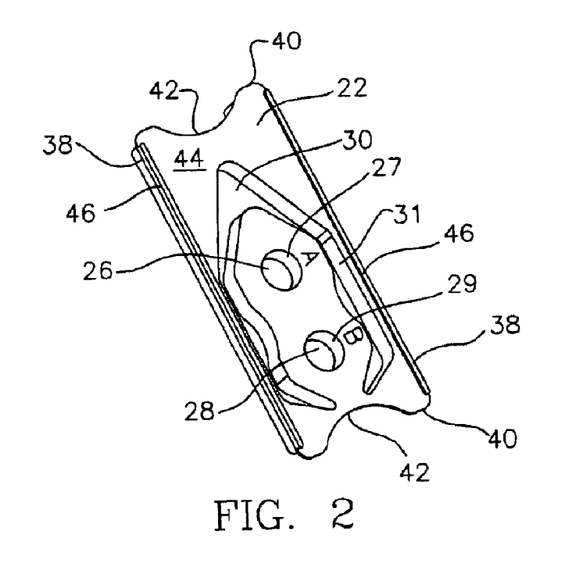
FIG. 2 is a perspective view of an embodiment of the carrier of the present invention.
Figure 3:
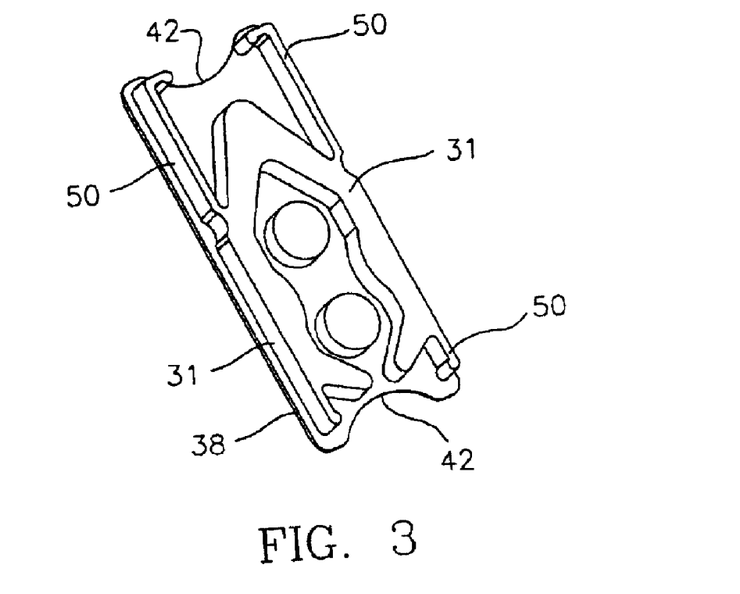
FIG. 3 is a perspective view of the bottom of an embodiment of the carrier of the present invention.

As shown in FIGS. 1–3, 5, and 12, the carrier 22 may include a first well 26 and a second well 28. The wells 26 and 28 may be defined, at least in part, by the walls 27 and 29, respectively. The wells 26 and 28 may be formed to have a variety of different depths and cross-sectional shapes, some variations of which are shown in FIGS. 5, 12–14 and 16. The wells 26 and 28 of the carrier 22 may be variously formed, and may have similar configurations or dissimilar configurations. As shown in FIGS. 3 and 13, the wells 26 and/or 28 may be generally frustoconical in shape, although the wells 26 and/or 28 may be cylindrical or otherwise shaped. The wells 26 and/or 28 may be formed so that, when viewed from the top of the carrier 22, the wells 26 and/or 28 have a non-circular shape, such as an elliptical, square, rectangular, D-shaped or any other shape.

Disposed within the first well 26 is a first composition 100 that may contain urea, such as urea in a finely powdered state with or without an anti-caking agent.

The first composition 100 is generally a dry or moisture-free composition containing urea in a powdered state. A second composition 102 may be disposed within the second well 28 and may include an indicator. The indicator may be configured to detect the presence of ammonia.

By maintaining urea in a powdered form separate from the indicator, the urea remains stable. Further, by maintaining the urea separate from the indicator, the handling requirements of the test system become less stringent. For instance, by maintaining both compositions separate, there is no need to refrigerate the compositions prior to use or during shipping.

Urea in a powdered state for use in the present invention is available from various commercial sources. The particle size of the urea contained in the first composition 100 may vary greatly.

In some embodiments, the mean particle size of the urea can be less than about 0.1 mm. In particular embodiments, the mean particle size of the urea can be less than 0.05 mm or less than about 0.01 mm. It should be understood, however, that even smaller particle sizes might be used. In some embodiments, the urea particles may have a mean particle size of less than about three microns, and in some embodiments may have a mean particle size of less than about 1 micron. By reducing the particle size, more surface area of urea is available for reaction with urease and the urea may adhere more effectively to the biopsy sample.

The urea particles can have a particle size distribution such that no particles present are larger than about 100 microns. Other embodiments may be used where the urea particles have a particle size distribution such that no particles present are larger than about 10 microns, or no greater than about 5 microns.

The particle size of the urea may be measured using any suitable technique. For instance, particle sizes can be measured using transmission electron microscopy (TEM). When using TEM, the average diameter of each particle is measured, followed by calculating the mean diameter of the urea particles in a particular group. The average diameter of each particle can be calculated by taking the average of the smallest diameter of the particle and the largest diameter of the particle. Besides transmission electron microscopy, light scattering can also be used to determine particle sizes. The mean particle size of the urea particles in a particular group is calculated by adding the sizes of the particles together and dividing by the number of particles.

Besides containing urea, the first composition 100 can also contain various other dry additives. For example, in one embodiment, if desired, an anti-caking agent can also be contained within the first composition. The anti-caking agent will prevent the fine urea powder from clumping or "caking". Any suitable anti-caking agent can be used in the present invention. For example, in one embodiment, fine silicon dioxide or fine sodium alumino silicate powder can be contained in the first composition. The weight per weight (w/w) ratio of urea/silicon dioxide contained in the first composition can be any ratio from 1/1 to 100/1. The particle size of the anti-caking agent may vary depending upon the particular embodiment. For example, the particle size of the anti-caking agent may be no greater than the particle size of the urea.

The second composition 102, which may be maintained separately from the first composition 100, may contain an indicator for indicating the presence of ammonia. Any suitable indicator can be present in the second composition 102. In one embodiment, a pH indicator can be used that indicates a change in pH. For example, various pH indicators are available that change color as the pH is increased.

When using a pH indicator, the pH of the second composition 102 may be less than about 6.5. The second composition 102 can have a pH that is consistent with mammalian tissue, which typically has a pH of about 6.5.

In this regard, the pH of the second composition 102 may be from about 4.0 to 6.5, and in some embodiments may be from about 4.5 to about 6.0. In this manner, when the second composition 102 is contacted with the biopsy sample containing urea, the pH of the second composition 102 will increase if the urea is being converted into ammonia. This rise in pH will then cause the pH indicator to signify a positive reading, such as by changing color. The pH of the second composition 102 can be adjusted to have a pH of from about 0.5 pH unit to about 2 pH units lower than necessary for a color change to occur.

When using a pH indicator, the indicator should undergo a color change or otherwise signify a positive reading when the pH of the second composition 102 rises above neutral, and, in particular, when the pH of the second composition rises above about 7.5. pH indicators useful in the present invention can include indicators that undergo a change in color over a pH range of from about 5.5 to about 9.0, and, in some embodiments, from about 6.5 to about 8.5.

One particular pH indicator that can be used in the present invention is phenol red. Phenol red changes from a yellow color to a red color as the pH of its surroundings increase. Phenol red is also referred to as phenolsulfonph-thalein. Other pH indicators that may be used in the present invention include p-nitro-phenol, bromothymol blue (dibromothymolsulfonph-thalein), neutral red (2-methl-3-amino-6-dimethylaminophenazine), quino-line blue (cyanine), cresol red (o-cresolsulfonphthalein), matacresol purple (m-cresolsulfonphthalein), thymol blue (thymolsulfonphthalein), bromocresol purple (4,4'-(3H-2,1-benzoxathiol-3-ylidene)bis[2-bromo-6-methylphenol]S,S-dioxide), chlorophenol red, bromocresol green (4,4'-(3H-2,1-benzoxathiol-3-ylidene)bis[2,6-dibromo-3-methylphenol] S,S-dioxide), and bromophenol blue (4,4'-(3H-2,1-benzoxathiol-3-ylidene)bis[2,6-dibromophenol]S,S-dioxide).

More than one type of pH indicator may be included in the second composition 102 in various embodiments of the present invention. In one embodiment, a combination of indicators can be used, such as described in U.S. Pat. No. 5,439,801 to Jackson, which is incorporated herein by reference. For example, in one embodiment, methyl red can be combined with bromthymol blue.

The second composition 102 can be made up entirely of the indicator or can include other ingredients. For example, in one embodiment, the indicator can be present in a gel-like material. In this regard, the indicator can be combined with a gelling agent so that the second composition 102 is in a semi-solid state under ambient conditions.

In one embodiment, the gelling agent can be agar. Agar is a polysaccharide complex that is extracted from agarocytes of certain algae. Agar is available from various commercial sources. For most applications, the agar or any other gelling agent used should be nonnutritive, i.e., does not support the growth of microorganisms.

Besides or in addition to a gelling agent, an indicator can also be combined with a buffering agent to maintain the pH of the second composition 102 within preset limits. The addition of a buffering agent is particularly beneficial when using a pH indicator to prevent against false readings. For example, as discussed above, the pH of the second composition 102 may be from about 4.0 to about 6.5 when using a pH indicator. A suitable pH adjuster can be used to maintain the pH of the composition within this range. pH adjusters suitable for this test include acids and buffering agents. The use of a pH adjuster depends upon the make-up of the second composition and the requirements of the test. For example, reduction of the amount of buffer in the second composition leads to a much faster reaction and a faster change in colors by the indicator, with the most rapid reaction rate occurring in the absence of a buffering agent, as compared to the reaction rate when using a large amount of a buffering agent. Thus, if a high reaction rate is required, the use of buffering agents as pH adjusters should be limited.

In general, any suitable pH adjuster can be used, depending upon the requirements of the test and the second composition, including the use of acids and buffering agents such as sodium citrate, phosphate-citrate, citric acid, sulfamic acid, sodium bisulfate, sodium acetate, sodium phosphate, and potassium phosphate.

Another ingredient that may be contained in the second composition 102 is a bactericide or bacteristat. The bactericide or bacteristat can be used to act as a preservative for any of the other ingredients or can be used to substantially inhibit the growth of urease-producing organisms to assist in preventing against false readings. Bactericides that can be used in the present invention include sodium azide, methyl paraben (methyl p-hydroxybenzoate), and propyl paraben (propyl p-hydroxybenzoate).

The amount of each ingredient added to the second composition 102 will depend upon the various circumstances and the desired result.

Besides maintaining the indicator as a liquid or in a gel state, the indicator can also be contained in an absorbent substrate, such as a substrate made from pulp fibers including cardboard or paper. In this embodiment, the second composition 102 can be dry and relatively moisture free. When using a paper substrate, however, extra water, such as distilled water, may need to be added to the second composition 102 in combination with the biopsy sample in order to provide enough moisture to activate the indicator.

The following is an example of one formulation that can be used as the second composition in the system of the present invention. The pH of the solid gel will be between 4 and 6.5 and particularly between 4.5 and 6.0.

| Ingredient | Amount |
|---|---|
| Agar (Extra Pure Grade) | 1.0–50.0 g |
| Citric Acid | 0.001–1.0 g |
| Phenol Red | 0.001–2.0 g |
| Methylhydroxy Benzoate | 0.01–100.0 g |
| Distilled Water | |

When forming a one liter batch of the above composition, the ingredients can be added in the following amounts.

| Ingredient | Reference | Amount |
|---|---|---|
| Agar (Extra Pure Grade) | Merck Catalog #1.01615.9025 | 15.0 g |
| Citric Acid | Merck Catalog #1.00247.1000 | 0.0145 g |
| Phenol Red | Merck Catalog #1.07241.0025 | 0.110 g |
| Methyl Paraben | Merck Catalog #1.06757.5000 | 2.0 g |
| Distilled Water | — | 1000 mL |

In producing the above gel composition, the distilled water is first heated to 95° C. The phenol red powder is added while stirring the distilled water, and the agar is added in small amounts while the mixture is maintained at 95° C. The citric acid and methyl paraben are then added to the mixture. The bulk liquid is cooled to 50° C. and dispensed in an amount of 0.2 mL into the second well of the present invention.

The first well of the container can contain 5 to 50 mg of the first composition, and optimally 30 mg of the resulting fine powder mixture. In the preparation of the urea mixture of the first composition for use in the first well, crystalline extra pure urea (Merck Catalog #1.08486.5000) is mixed with silicon dioxide (Sigma Catalog #S-5631) at a weight-to-weight ratio from 1:1 to 100:1, and in one embodiment in a weight-to-weight ratio of 2:1. The mixture is subject to grinding until a fine powder mixture results.

Figure 4:
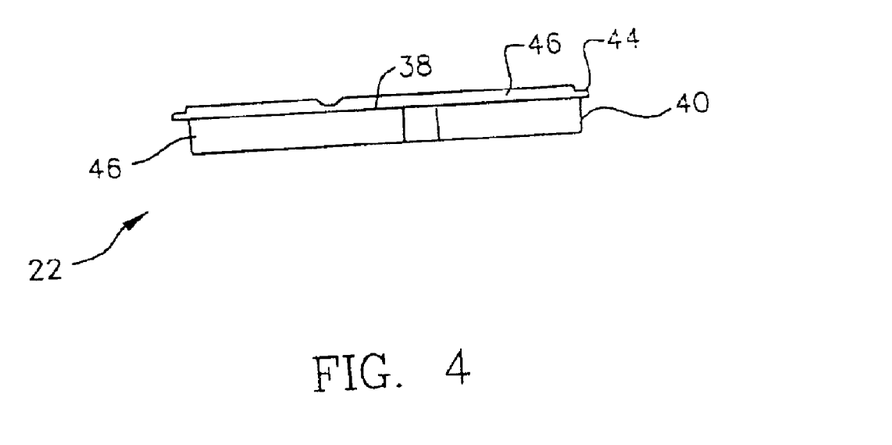
FIG. 4 is a side view of an embodiment of the carrier of the present invention.

Another embodiment of the present invention is illustrated in FIG. 4. In this embodiment, instead of containing two separate wells and two separate compositions, the urease testing device contains a single composition in a dry powdered state. Specifically, in this embodiment, the urease indicating composition contains dry powdered urea combined with a dry powdered indicator.

Figure 17:
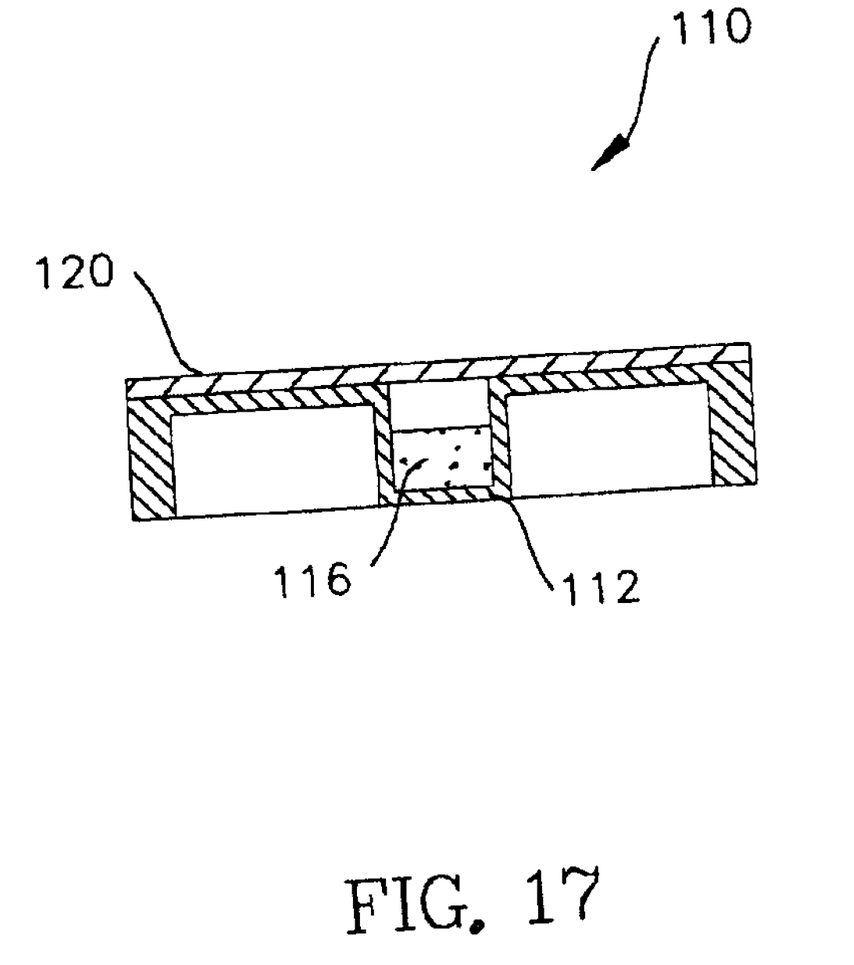
FIG. 17 is a cross-sectional view of an alternate embodiment of the present invention.
Figure 18:
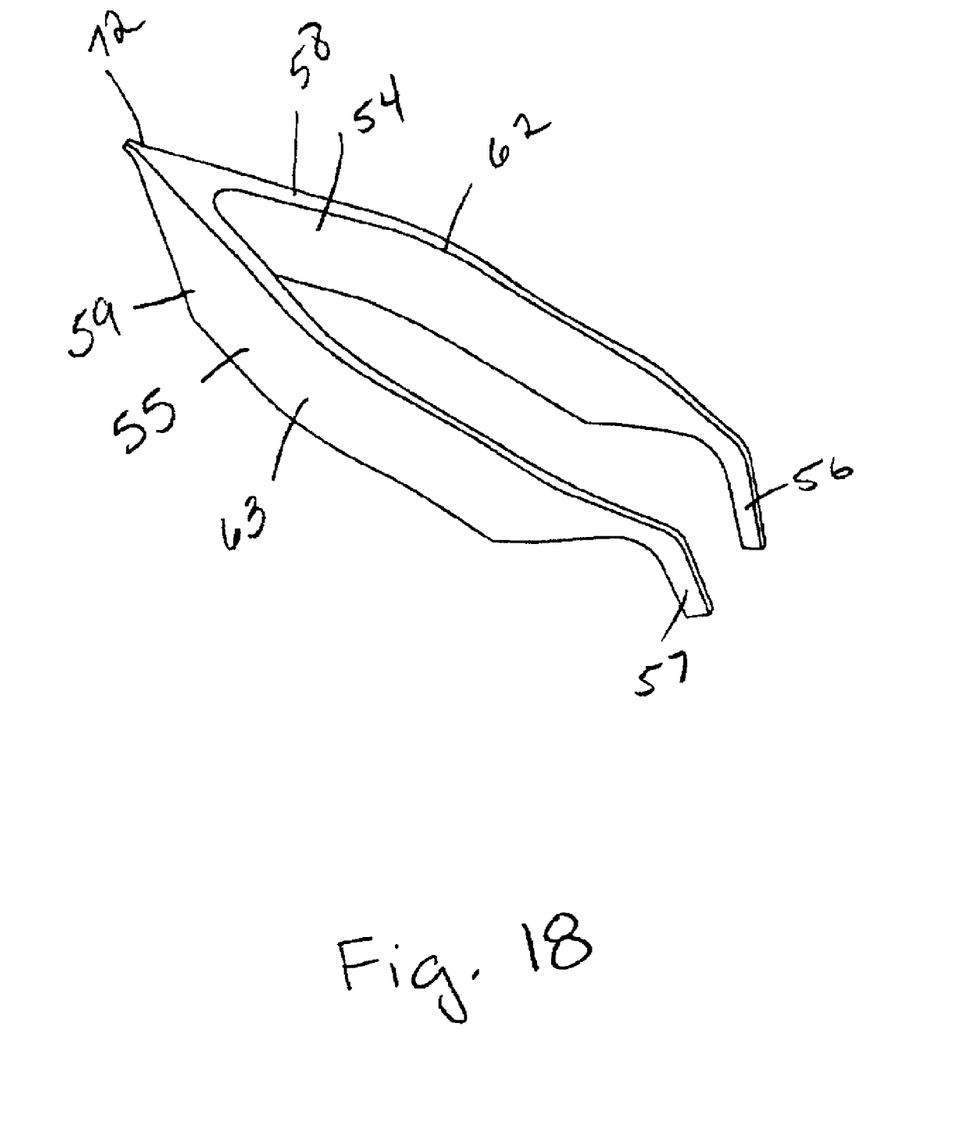
FIG. 18 is a perspective view of another embodiment of the specimen-handling tool of the present invention.

For example, as shown in FIG. 17, a urease testing device generally 110 includes a single well 112 covered by a peelable plastic film 120. In accordance with the present invention, the well 112 includes a urease indicating composition 116, which contains a powdered mixture of urea and an indicator.

The powdered urea contained within the well 120 can be a urea as described above having an average particle size of less than about 0.1 mm, particularly less than about 0.05 mm, and more particularly less than about 0.01 mm. Combined with the powdered urea is a dry or powdered indicator, such as a pH indicator. In general, any suitable dry indicator can be present in the composition, such as any of the above-described indicators. The amount if indicator contained within the composition 116 will generally depend upon the particular indicator chosen. Specifically, the indicator should be present in the composition 116 in an amount sufficient to show a color change when the composition 116 is contacted with urease present in a biopsy sample.

In this embodiment, the biopsy sample is placed in the well and mixed with the powdered composition. Any moisture present in the biopsy sample can be used to activate the urea and the indicator. If necessary, however, an aqueous solution, such as distilled water, can be added with the biopsy sample. If urease is present in the biopsy sample, the urease will convert the urea into ammonia which, in turn, will cause the indicator to indicate a positive result, such as by changing color.

If desired, an anti-caking agent as described above can also be contained in the dry powdered composition. In this embodiment, however, a pH adjuster or a bactericide will most likely not be needed, although both ingredients can be contained in the composition if desired.

EXAMPLE

The following example was performed in order to demonstrate the stability of a urease testing device made in accordance with the present invention.

A test slide according to the present invention was prepared containing the urea composition and the indicator gel composition described above. The indicator gel composition, however, did not contain the methyl paraben bactericide or the citric acid pH adjuster.

Specifically, the gel composition contained the following:

| Ingredient | Amount |
| --- | --- |
| Extra Pure Grade Agar | 1.4941 g |
| Phenol Red | 0.0110 g |
| Distilled Water | 100.00 mL |

The shelf life of the above prepared slide was then compared with the shelf life of a commercial product marketed under the name CLO-TEST by Ballard Medical/Kimberly Clark of Draper, Utah. The CLO-TEST product includes a urease indicator composition which contains a mixture of urea and an indicator in a gel as described in U.S. Pat. No. 4,748,113.

Three test slides made according to the present invention were compared with three samples of the CLO-TEST product. A standardized CLO-TEST Color Chart developed prior to the experiment was used to assign numerical scores to the color of the samples during the experiment.

The slides were affixed to a polystyrene box introduced into a chamber set at 37° C., 100% relative humidity, and 10% carbon dioxide. Photographs were taken every 24 hours for a period of 45 days, which were then assessed and given a score using the CLO-TEST Color Chart. Using color readings with scores of equal to or greater than 4 as unusable, the CLO-TEST samples were deemed unusable on day 4, while the test slides of the present invention were still viable on day 45.

The shelf life of the test slide of the present invention was also tested with an artificial biopsy by means of a tissue sample containing deliberately introduced urease. The artificial biopsy sample was placed in the first well containing the powdered urea. The sample was coated with urea, and then placed in the second well containing the indicator gel composition. Observations of the color change of the gel revealed it was still viable for the detection of ammonia after 39 days, when the gel was checked.

Figure 12:
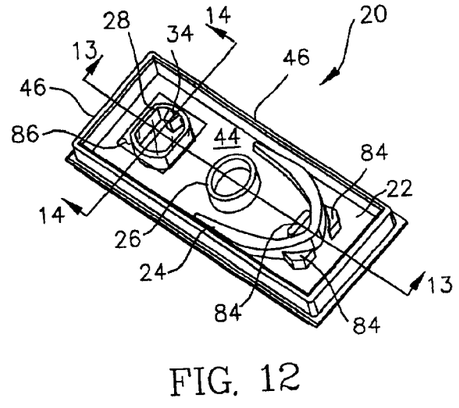
FIG. 12 is a perspective view of another embodiment of the system, carrier and specimen-handling tool of the present invention.
Figure 13:
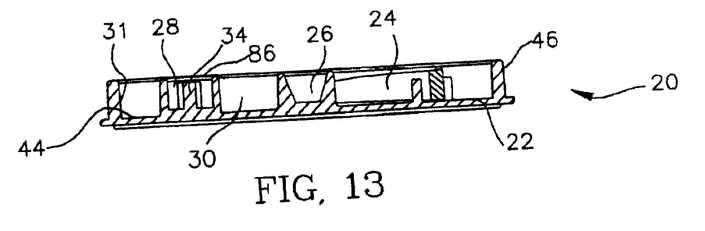
FIG. 13 is a cross-sectional view of the embodiment depicted in FIG. 12, taken along line 13—13.
Figure 14:
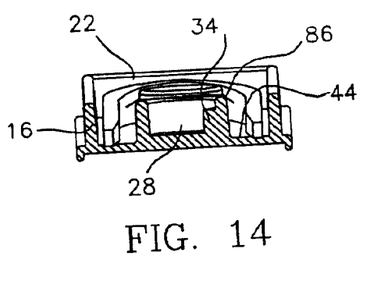
FIG. 14 is a perspective cross-sectional view of the embodiment depicted in FIG. 12, taken along line 14—14.

One or more projecting members, such as the projecting member 34 that is shown in FIGS. 12–14, may be disposed within one or both of the wells 26 and 28. At least a portion of the projecting member 34 may be disposed outside of the interior of the wells 26 and/or 28. The projecting member 34 may be integrally formed with the walls 27 and 29, or may be attached to the walls 27 and/or 29. Such projecting members 34 may be configured to assist removal of the specimen such as, for example, a biopsy specimen, from the specimen-handling tool 24.

These projecting members 34 may be configured to assist the user in accurately positioning a specimen within the well 26 or 28.

The wells 26 and 28 may also include a step such as the step 32 that is depicted in FIG. 13.

Figure 5:
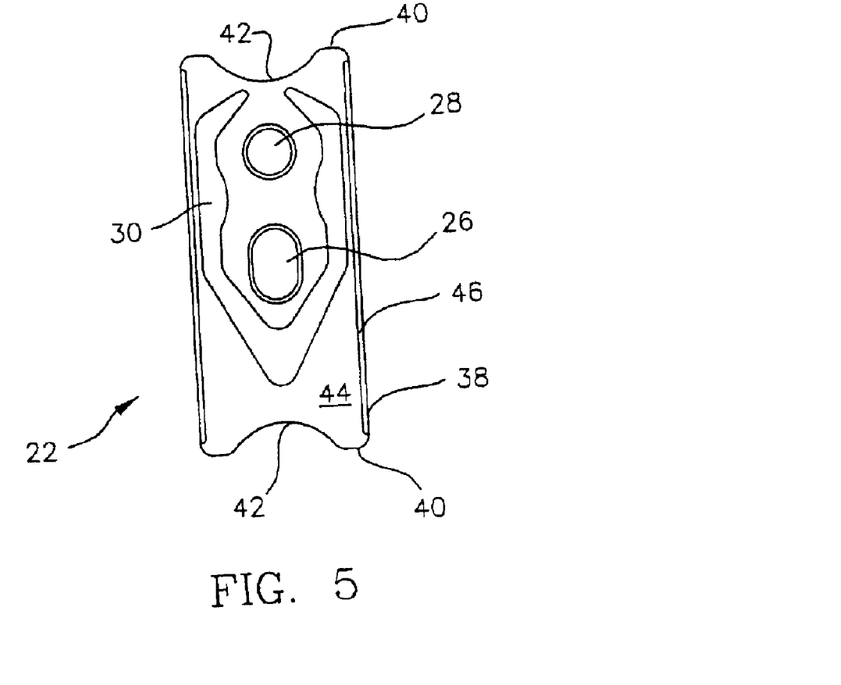
FIG. 5 is a top view of another embodiment of the carrier of the present invention.

The carrier 22 may have many different overall exterior shapes, such as, for example, the generally rectangular shape as shown in FIGS. 1, 2 and 5. The carrier 22 may be alternately shaped, such as, for example, square, oblong, triangular, and the like. The carrier 22 may, as shown in FIGS. 1–3, include two elongated sides 38, two ends 40 and a surface 44. The ends 40 may be configured to be easily grasped by a user and one, none or both of the ends 40 may include an arcuate portion 42 as shown in FIGS. 1–5.

As shown in FIGS. 1, 2, 4 and 5, the carrier 22 may include a surface 44. The first and/or second wells 26 and 28, respectively, may be configured to extend downwardly from the surface 44. As shown in FIGS. 1 and 2, the carrier 22 may also include a cavity 30. In a similar manner, the cavity 30 may be configured to extend downwardly from the surface 44, as shown in FIGS. 1, 2 and 5. As shown in FIGS. 12–14, one or both of the wells 26 and 28 and/or the cavity 30 may be formed so as to extend upwardly from at least a portion of the surface 44.

A mechanism by which a user may manipulate a sample of tissue, such as, for example, the specimen handling tool 24 such as that shown in FIGS. 1 and 6–11, may also be included in particular embodiments of the diagnostic system 20 of the present invention. The specimen-handling tool 24 may be disposed within the cavity 30.

The cavity 30 may, as shown in FIGS. 1–3, be configured so that it is disposed about at least a portion of one of the first and/or second wells 26 and 28, respectively. The carrier 22 may also be configured so that a specimen handling tool 24 may be otherwise retained in the carrier 22 so that it is disposed about at least a portion of one of the first and/or second wells 26 and 28, respectively. As shown in FIGS. 12 and 13, the carrier 22 may be configured so that the specimen-handling tool 24 is secured in a particular position by one or more ribs 84. The specimen-handling tool 24 may be removably attached to the carrier 22 by one or more locking arms, breakaway tabs, adhesive, or the like.

One or more rails 46 may be included in selected embodiments of the present invention and may be disposed on the carrier 22 so that the rails extend upwardly along at least a portion of the surface 44. One or more rails 46 may also be configured to extend outwardly from the carrier 22. At least one gap 48 may be formed in one of the rails 46 that extend along a portion of the carrier 22.

As shown in FIG. 3, one or more supports 50 may be provided which extend downwardly from the surface 44. As seen in FIG. 3, the supports 50 may be attached to the wall (or walls) 31 that form at least a portion of the cavity 30. The supports 50 may extend outwardly from the wall 31 to permit the carrier 22 to rest in a stable position on a horizontal or other surface. The rails 46 and the supports 50 may be configured to enable the carrier 22 to be automatically processed through a variety of equipment.

If desired, the surface 44 may be configured so that various indicia, such as letters, numbers, symbols and other characters, may be placed onto or formed into the surface 44. For example, and as shown in FIG. 2, each well 26 and/or 28 may be given a particular designation, such as A or B, and that designation may be printed upon the surface 44.

The carrier 22 may be formed from a variety of materials, including, for example, polycarbonate, polystyrene, polypropylene, polyethylene, polyvinylchloride, or any other type of polyolefin.

Particular embodiments of the specimen-handling tool 24 are shown in FIGS. 6–11 and 18. The specimen-handling tool 24 may include, as shown in FIGS. 6–9, a pair of cooperating arms 54 and 55. Each arm 54 and 55 may include a tip portion 56 and 57, respectively. The arms 54 and 55 may each also include a rear portion 58 and 59, respectively. The arms 54 and 55 may be joined to each other at their rear portions 58 and 59, respectively, forming a joined end 60. The joined end 60 may be configured to assist the user in accomplishing particular tasks, such as, for example, manipulating a specimen, removing a plug 86 from one of the first and/or second wells 26 and 28, respectively, as well as other tasks. The outermost portion of the joined end 60 may be variously configured, and may be formed as a narrow projection, such as that shown in is FIG. 10.

Figure 8:
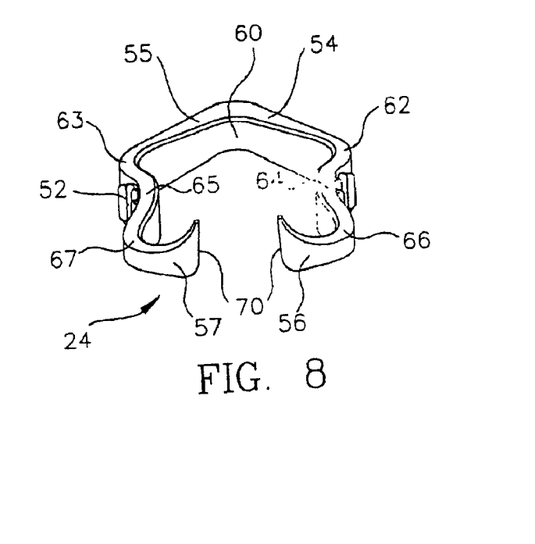
FIG. 8 is another perspective view of an embodiment of the specimen-handling tool of the present invention.
Figure 9:
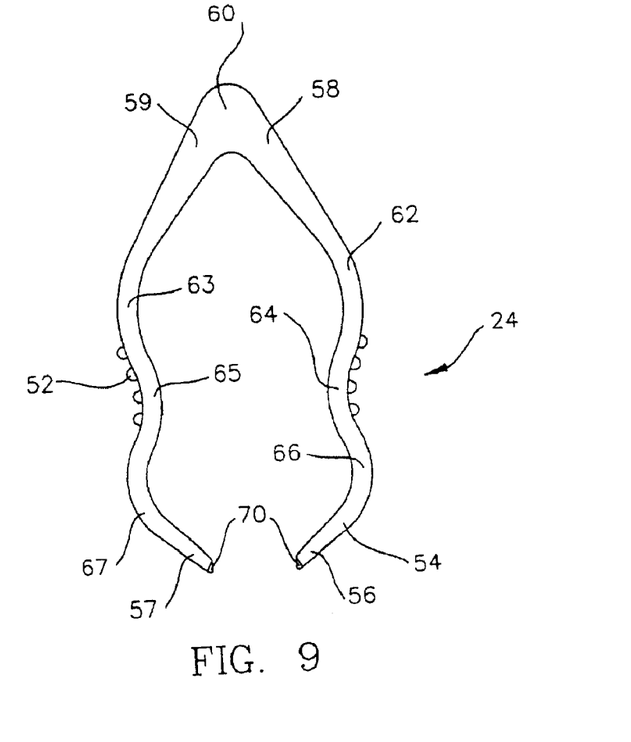
FIG. 9 is a top view of an embodiment of the specimen-handling tool of the present invention that is depicted in FIG. 8.

As seen in FIGS. 8 and 9, each arm 54 and 55 may also include a rearward arcuate portion 62 and 63, respectively, and a forward arcuate portion 66 and 67, respectively. Disposed between each rearward arcuate portion 62 and 63 and its corresponding forward arcuate portion 66 and 67, respectively, is an intermediate arcuate portion 64 and 65, respectively. The arcuate portions 62-64-66 and 63-65-67 of each arm 54 and 55, respectively, may be configured so that the area disposed between the arms 54 and 55 is approximately hourglass in shape. In such an embodiment, the rearward arcuate portions 62 and 63 and forward arcuate portions 66 and 67 curve outwardly, and the intermediate arcuate portions 64 and 65 curve inwardly.

The intermediate arcuate portions 64 and 65 may be formed so that a user may more easily grip these portions. As shown in FIG. 6, one or more ribs 52 may be positioned on the outer surface of the intermediate arcuate portions 64 and 65. Alternately, a portion of the arms 54 and/or 55 may have a roughened texture to enable a user to more effectively grasp and manipulate the specimen-handling tool 24, such as is shown in FIG. 10 at 51.

Figure 11:
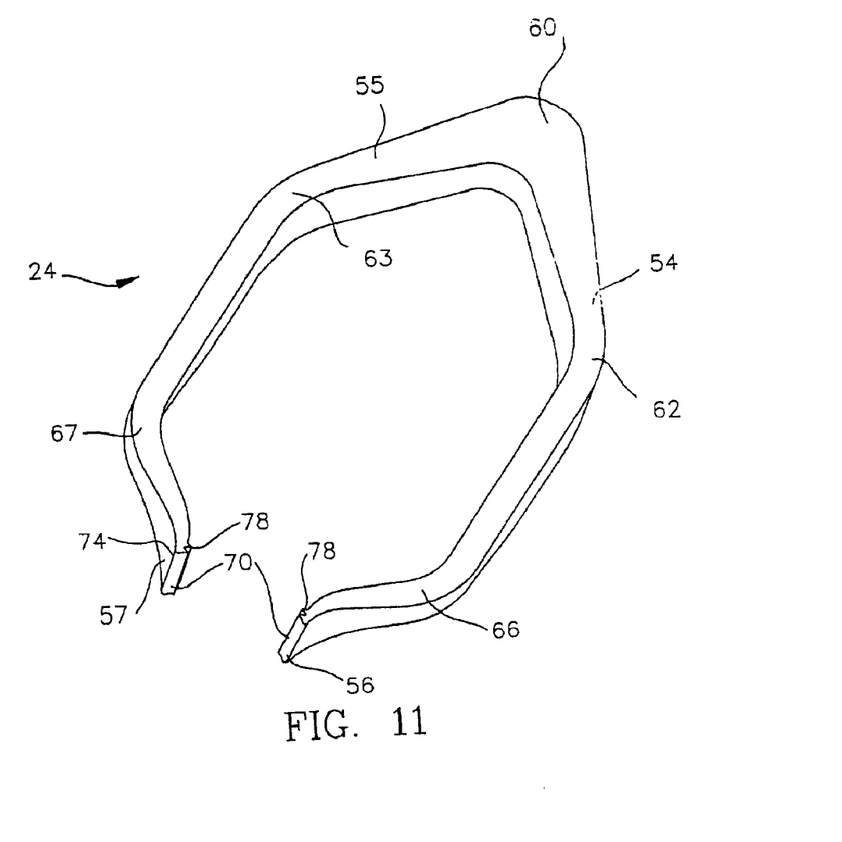
FIG. 11 is a perspective view of still another embodiment of the specimen-handling tool of the present invention.

The arms 54 and/or 55 may include fewer or more arcuate portions than the three arcuate portions described above, such as the specimen-handling tool shown in FIG. 11. The arcuate portions of the arms 54 and/or 55 may have a more or less pronounced arcuate shape than what is depicted in FIG. 6. For example and as shown in FIGS. 10–12 and 18, other configurations of the arms 54 and 55 may be used in the specimen-handling tool 24.

The tip portions 56 and 57 may be variously formed to enable a user to manipulate a specimen. The tip portions 56 and 57 may be formed to include a surface such as the surfaces 70. The surfaces 70 may be variously shaped and, in particular, one or both of the surfaces 70 may be curved (as shown in FIG. 10) or flat (as shown in FIG. 6). The surfaces 70 may be rough or smooth. Also, structures such as the ridges 78 that are depicted in FIG. 11 may also be positioned on one or more of the surfaces 70. The surfaces 70 may be disposed so that they are at least somewhat facing each other, thereby enabling a user to grasp a specimen and hold it between the surfaces 70. As shown in FIG. 10, the tip portions 56 and/or 57 may curve outwardly, and may, in some embodiments such as is shown in FIG. 11, end in a relatively sharp edge 74. One or both of the tip portions 56 and 57 may include a point, such as the point 80 shown in FIG. 10 or a fork 82, also shown in FIG. 10, or any number of other configurations.

The specimen-handling tool may be formed from a variety of materials, including, for example, polycarbonate, polystyrene, polypropylene, polyethylene, polyvinylchloride, or any other type of polyolefin.

Figure 16:
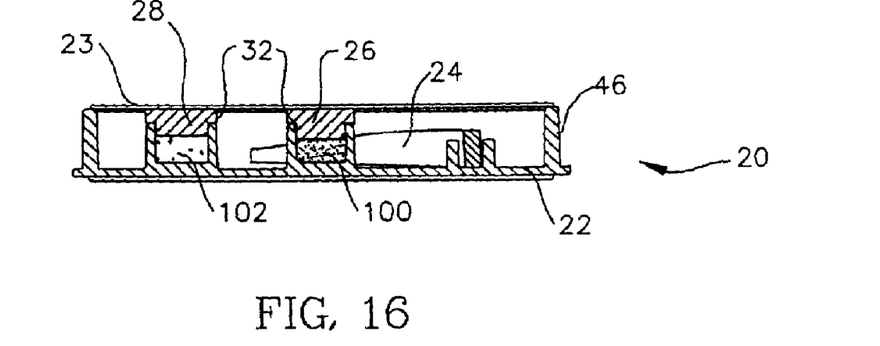
FIG. 16 is a cross-sectional view of the embodiment depicted in FIG. 15, taken along line 16—16.

Referring now to FIGS. 15 and 16, an overlying member 23 may be disposed over at least a portion of the surface 44 of the carrier 22. At least a portion of the cavity 30 may be formed by the wall 31. The overlying member 23 may take the form of an adhesive-backed label that adheres to at least a portion of the surface 44. The overlying member 23 may overly any combination of the first well 26, the second well 28 and the cavity 30.

The overlying member 23 may also be used to seal the first and second wells 26 and 28, respectively. In some embodiments, the overlying member may be used to regulate the rate of water vapor transmission to and from the wells 26 and 28 of the carrier 22. The overlying member 23 may also be configured so that, if the overlying member 23 is removed prematurely or inadvertently, it may be easily reapplied to the carrier 22 so that the wells 26 and 28 may be resealed.

The overlying member 23 may also be used to retain the specimen-handling tool 24 within the cavity 30. The overlying member 23 may also be configured only to retain the specimen-handling tool 24 within the cavity 30. In some embodiments, the overlying member 23 may be adhered to at least a portion of the specimen-handling tool 24 so that, when the overlying member 23 is removed form the carrier 22, the specimen-handling tool 24 is also removed from the carrier 22. Although this may be accomplished in many different ways, the intermediate arcuate portions 64 and 65 may, when the specimen-handling tool 24 is positioned within the cavity 30, be level with or rise slightly above the surface 44 so as to contact and be adhered to the overlying member 23.

As shown in FIG. 16, a plug 86 may also be used to at least partially seal each well 26 and 28. In such a configuration, the overlying member 23 does not need to seal the well that contains the plug 86, but may merely be positioned above the well 26 and/or 28. The plug 86 may be formed from a variety of materials, including, for example, rubber, wax, silicone, or any of a variety of plastics. In some embodiments, a film cover 86, shown in FIG. 14, may also be applied to a portion of the carrier 22, such as, for example, the well 28.

In some embodiments, the overlying member 23 may be adhered or otherwise connected to one or more of the plugs 86 so that, when the overlying member 23 is separated from the carrier 22, one or more of the plugs 86 may also be removed. The plug 86 may also be removed with the specimen-handling tool.

To perform a urease test using the device shown in FIG. 1, a biopsy sample is first taken from the lining of the gastrointestinal tract of a patient, such as from the lining of the stomach. The biopsy sample can be taken during an endoscopic procedure using biopsy forceps. The overlying member 23 may be peeled back to expose the first composition 100 in the first well 26. The biopsy sample is then contacted with the first composition 100, causing the urea powder to stick to the biopsy sample. The biopsy sample can be rolled in the first composition 100 much like the process of "flouring" a food product prior to cooking.

Once the first composition 100 has coated the biopsy sample, the biopsy sample may then be contacted with the second composition 102 which contains an indicator, the second composition 102 being located in the second well 28. Once contacted with the second composition 102, the powdered urea on the surface of the biopsy sample is moistened and activated by the second composition 102. Once moistened, the urea powder becomes available in greater amounts to any urease enzyme present in the biopsy sample. If present, the urease converts the urea into ammonia or ammonium carbonate. The indicator present in the second composition 102 indicates the presence of ammonia to signify a positive test for urease. For example, in one embodiment, the indicator can be a pH indicator that changes color when the pH of its environment is increased.

As used herein, any given range is intended to include any and all lesser included ranges. For example, a range of from 45–90 would also include the ranges of from 50–90, 45–30, 46–89, etc. Thus, the range of 95% to 99.999% also includes, for example, the ranges of 96% to 99.1%, 96.3% to 99.7%, and 99.91 to 99.999%.

The invention may be embodied in other specific forms without departing from the scope and spirit of the inventive characteristics thereof. The present embodiments therefore are to be considered in all respects as illustrative and not restrictive, the scope of the invention being indicated by the appended claims rather than by the foregoing description, and all changes which come within the meaning and range of equivalency of the claims are therefore intended to be embraced therein.

It is emphasized that the Abstract is provided to comply with the rules requiring an abstract that will allow a searcher or other reader to quickly ascertain the subject matter of the technical disclosure. It is submitted with the understanding that it will not be used to interpret or limit the scope or meaning of the claims. 37 CFR 1.72(b).

We claim:

1. A method for detecting the presence of urease in a gastrointestinal system comprising:
    grasping a sample of gastric material with a specimen-handling tool;
    contacting the gastric material with a first composition disposed in a first well of a carrier, the first composition comprising a powder-form urea, the urea being converted into ammonia when contacted with urease; and
    thereafter contacting the gastric material with a second composition disposed in a second well of a carrier, the second composition comprising an indicator, the indicator being configured to indicate the presence of ammonia thereby indicating the presence of urease in the gastric material;
    wherein, the first composition is isolated from the second composition; and
    wherein, said isolated first composition remains stable at about room temperature.

2. A method as defined in claim 1, wherein said stability provides a shelf life of about 40 days.

3. A method as defined in claim 2, wherein the urea has a mean particle size of less than about 0.1 mm.

4. A method as defined in claim 1, wherein the first composition further comprises an anti-caking agent.

5. A method as defined in claim 1, wherein the second composition comprises a gel.

6. A method as defined in claim 1, wherein the second composition comprises agar in addition to the indicator.

7. A method as defined in claim 1, wherein the indicator comprises a pH indicator that changes color when the pH is increased.

8. A method as defined in claim 1, wherein the second composition further comprises a bactericide.

9. A method as defined in claim 1, wherein the indicator comprising phenol red.

10. A method as defined in claim 1, wherein the second composition further comprises a buffering agent.

11. A method as defined in claim 2, wherein the second composition further comprises agar and a buffering agent.

12. A method as defined in claim 1, wherein the gastric material is contacted with the first composition such that at least a portion of the urea is combined with the gastric material prior to being contacted with the second composition.

13. A method as defined in claim 1, further comprising providing a carrier having a specimen-handling tool.

14. A method as defined in claim 13, the specimen-handling tool being disposed within at least a portion of the carrier.

15. A method as defined in claim 1, further comprising providing a carrier having a first well and a second well.

16. A method for detecting the presence of urease in a gastrointestinal system comprising:
    grasping a sample of gastric material with a specimen-handling tool having a pair of arms;
    contacting the gastric material with a first composition disposed in a first well of a carrier, the first composition comprising urea, the urea being present as a powder and being converted into ammonia when contacted with urease, the urea having a mean particle size of less than about 0.1 mm, the gastric material being contacted with the first composition such that at least a portion of the urea is combined with the gastric material; and
    thereafter contacting the gastric material with a second composition disposed in a second well of a carrier, the second composition comprising a buffering agent and a pH indicator that changes color when the pH of the second composition is increased, the indicator being configured to indicate the presence of ammonia thereby indicating the presence of urease in the gastric material.

* * * * *